United States Patent [19]

Donovan et al.

[11] Patent Number: 5,356,372
[45] Date of Patent: Oct. 18, 1994

[54] OCCLUSIVE PRESSURE-REDUCING WOUND DRESSING

[75] Inventors: Maura G. Donovan, St. Paul; Matthew A. Bergan, Brooklyn Park, both of Minn.

[73] Assignee: Ludlow Corporation, Exeter, N.H.

[21] Appl. No.: 160,568

[22] Filed: Dec. 1, 1993

[51] Int. Cl.⁵ ............................................. A61F 5/34
[52] U.S. Cl. .................... 602/58; 604/304; 604/307; 602/41; 602/42; 602/43
[58] Field of Search ................. 602/41–48, 602/56–59; 604/358, 368, 369, 385.1, 304, 307; 5/481, 981

[56] References Cited

U.S. PATENT DOCUMENTS

| | | |
|---|---|---|
| 239,159 | 3/1881 | Gaussen ........................ 5/481 |
| 3,674,027 | 7/1972 | Fleischmajer ................. 604/304 |
| 3,927,669 | 12/1975 | Glatt . |
| 3,978,855 | 9/1976 | McRae . |
| 4,005,709 | 2/1977 | Laerdal . |
| 4,146,027 | 3/1979 | Hoey . |
| 4,212,296 | 7/1980 | Schaar . |
| 4,360,015 | 11/1982 | Mayer . |
| 4,377,159 | 3/1983 | Hansen . |
| 4,538,603 | 9/1985 | Pawelchak . |
| 4,625,720 | 12/1986 | Lock . |
| 4,726,364 | 2/1988 | Wylan . |
| 4,730,611 | 3/1988 | Lamb . |
| 4,733,659 | 3/1988 | Edenbaum . |
| 4,738,257 | 4/1988 | Meyer . |
| 4,743,499 | 5/1988 | Volke . |
| 4,753,231 | 6/1988 | Lang . |
| 4,773,408 | 9/1988 | Cilento . |
| 4,773,409 | 9/1988 | Cilento . |
| 4,793,337 | 12/1988 | Freeman . |
| 4,904,247 | 2/1990 | Therriault . |
| 4,909,244 | 3/1990 | Quarfoot . |
| 4,972,535 | 11/1990 | Goldman ........................ 5/481 |
| 4,977,892 | 12/1990 | Ewall . |
| 4,995,382 | 2/1991 | Lang . |
| 5,025,783 | 6/1991 | Lamb . |
| 5,059,424 | 10/1991 | Cartmell . |
| 5,060,662 | 10/1991 | Farnswoth . |
| 5,104,660 | 4/1992 | Chvapil . |
| 5,109,874 | 5/1992 | Bellingham . |
| 5,112,618 | 5/1992 | Cartmell . |
| 5,147,338 | 9/1992 | Lang . |
| 5,154,928 | 10/1992 | Andrews . |
| 5,156,601 | 10/1992 | Lorenz et al. ................. 604/307 |
| 5,160,328 | 11/1992 | Cartmell . |
| 5,170,781 | 12/1992 | Loomis ........................ 602/42 |
| 5,176,663 | 1/1993 | Svedman . |

FOREIGN PATENT DOCUMENTS 0076426  7/1894  Fed. Rep. of Germany ...... 604/304

Primary Examiner—Randall L. Green
Assistant Examiner—P. Zuttarelli
Attorney, Agent, or Firm—Richard H. Kosakowski

[57] ABSTRACT

An occlusive, pressure-reducing wound dressing with a multi-layer laminate construction providing one easy-to-apply dressing. The occlusive pressure-reducing dressing includes an occlusive, wound-contacting layer made of a biologically compatible polymer. A pressure-reducing layer is joined at a bottom surface to the occlusive layer. The pressure-reducing layer is comprised of a soft, air-containing material such as a foam or an air-entrapping film which has a top surface shaped to provide a progressive rate of resistance to compressive force applied to the pressure-reducing layer and which allows the pressure-reducing layer to conform to curved body surfaces. The occlusive portion of the dressing therefore provides a moist environment and a barrier against infection while the pressure-reducing portion or component minimizes interaction between the wound and any supporing surface in contact therewith.

20 Claims, 3 Drawing Sheets

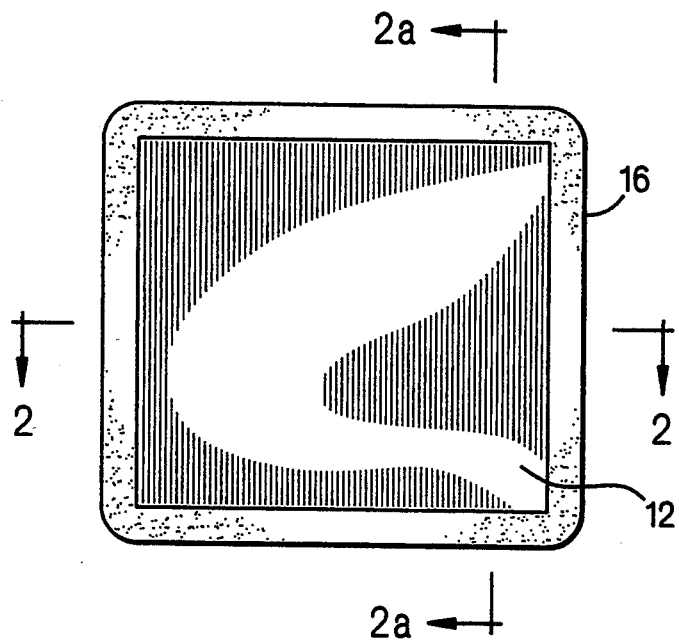
FIG. 1
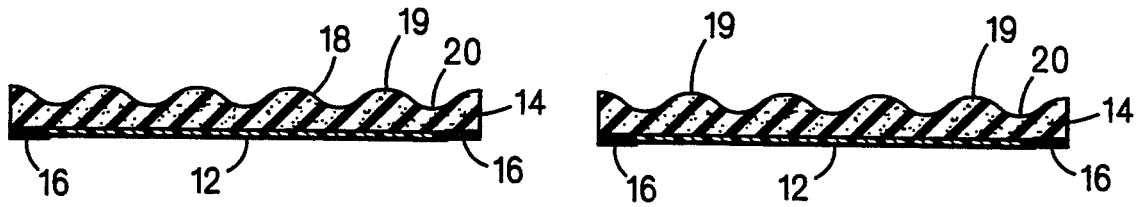
FIG. 2
FIG. 2a
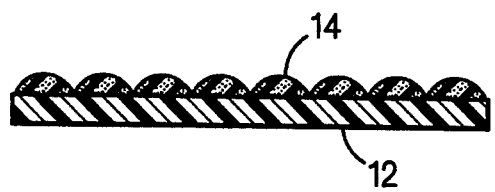
FIG. 3

OCCLUSIVE PRESSURE-REDUCING WOUND DRESSING

BACKGROUND OF THE INVENTION

The present invention relates to wound dressings and more specifically to those which alleviate pressure ulcers. Pressure ulcers develop in situations in which the skin is in contact over extended periods of time with supporting surfaces such as a mattress. More specifically, it has been shown that any external or internal force applied to bony prominences of greater than 32 mmHg can contribute to capillary shutdown. When capillary flow is interrupted by external pressure, hypoxemia will lead to tissue destruction and tissue death. Increased pressures for a short duration are as harmful to tissue as low pressure for long periods.

Currently, it is common practice to apply a separate occlusive dressing to such wounds and then to augment the dressing with an air bed or other pressure-reducing device. Occlusive dressings by themselves do not alleviate pressure. Pressure-reducing devices alone do not provide the necessary healing environment. Also, pressure-reducing features can, by their size and stiffness, actually increase the pressure on a wound when applied over a curved body surface.

It is therefore an object of the present invention to provide a wound dressing which includes both occlusive and pressure-reducing features.

It is yet another object of the invention to provide a wound dressing which includes within the pressure-reducing feature the ability to conform to curved body surfaces.

It is yet another object to provide a wound dressing which is easily applied by a health care worker.

SUMMARY OF THE INVENTION

The present invention combines an occlusive component with a pressure-reducing component into a multilayer laminate construction providing one easy-to-apply dressing. The occlusive pressure-reducing dressing includes an occlusive, wound-contacting layer made of a biologically compatible polymer which is preferably either a hydrogel or hydrocolloid. A pressure-reducing layer is joined at a bottom surface to the occlusive layer. The pressure-reducing layer is comprised of an air-containing material such as a foam or an air-entrapping film which has a top surface shaped in a contour which allows the pressure-reducing layer to conform readily to curved body surfaces and to provide a progressive rate of resistance to compressive forces applied to the contoured top surface of the pressure reducing layer. To secure the wound dressing onto the patient, an adhesive portion can be carried by the pressure reducing layer or the pressure reducing layer can be provided with a thinned portion at a peripheral edge which accepts tape for securing to the skin of a patient. Preferably, the material selected for the pressure reducing layer has uniform compressive properties. The top surface of the pressure-reducing layer is shaped to include a plurality of raised and depressed portions. This provides a lower overall resistance to an applied compressive force when the pressure-reducing layer is initially compressed. It also provides a greater overall resistance to a greater applied compressive force. Also preferably, the contour of the top surface includes valleys or crease points extending across the top surface of pressure-reducing layer to enable the pressure-reducing layer to conform to curved body surfaces and most preferably the valleys or crease points are arranged in a substantially right-angled orientation to provide the pressure-reducing layer to conform to curved body surfaces in multiple directions. The occlusive portion of the dressing therefore provides a moist environment and a barrier against infection while the pressure-reducing portion or component minimizes interaction between the wound and any supporting surface in contact therewith.

BRIEF DESCRIPTION OF THE FIGURES

FIG. 1 is a bottom plan view of the skin contacting surface area or underside of an "island" style dressing according to the invention.

FIG. 2 is a cross-sectional view taken along line 2—2 of FIG. 1 (underside down).

FIG. 2a is a cross-sectional view taken along line 2a—2a of FIG. 1 (underside down).

FIGS. 3 is a cross-sectional view of a flush cut dressing.

DETAILED DESCRIPTION OF THE INVENTION

Figure 4:
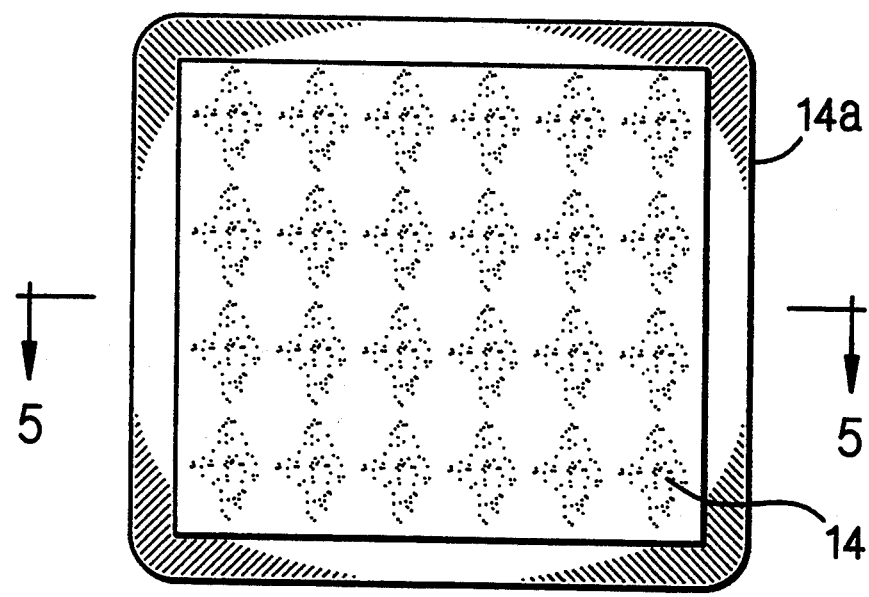
FIG. 4 is a top plan view of the top or outer surface of a dressing similar to that shown in FIG. 1 including a tape-down area on its perimeter.

As illustrated in FIGS. 1, 2 and 2a, the invention consists of an occlusive dressing formed of a wound contacting layer 12 (occlusive layer) in combination with a pressure-reducing layer or cushioning component in the form of layer 14. The wound contacting layer 12 constitutes the occlusive portion of the dressing and may consist of a biologically compatible polymer such as a hydrogel, hydrocolloid, or other comparable substance (many of which are well known in the an), or a combination thereof. An example of such a hydrogel is a polyvinylalcohol/polyvinylpyrrolidone based gel such as that which is described in U.S. Pat. No. 4,593,053, the entire content of which is incorporated herein by reference. The pressure-reducing layer 14 may take the form of an air-containing material such as a dense foam, a reticulated foam, an air-entrapping material such as bubble wrap, or a spongy material. The substance should be soft, yet resilient and sufficiently thick to deform on contact and thereby reduce the transmission of pressure, i.e., steady, compressive force to the wound.

The embodiment of FIGS. 1, 2 and 2a illustrates an adhesive layer 16 that can be applied to the pressure reducing layer 14 as shown in FIG. 2. Any medical grade adhesive which is compatible with layer 14 and which is not deleterious to skin can be applied. These adhesives are well known to those skilled in the art.

FIG. 3 illustrates a flush cut version of the device without adhesive including occlusive layer 12 and pressure reducing layer 14.

The pressure-reducing layer 14 comprises at a top surface 18 a contour which allows the pressure-reducing layer to conform to curved body surfaces. Preferably, the material selected for the pressure reducing layer 14 has uniform compressive properties. The top surface 18 of the pressure-reducing layer 14 is shaped to include a plurality of elevated domains 19 and lowered domains 20. This contoured surface provides a lower overall resistance to larger applied compressive force when the pressure-reducing layer 14 is initially compressed. It also allows the layer 14 to provide a greater overall compressive force. In addition to providing a progressive rate of resistance for the pressure-reducing layer, the same contouring of elevated domains 19 and lowered domains 20 can also provide the flexibility required in the pressure-reducing layer to conform to curved body surfaces. The top surface 18 can therefore be contoured as an "egg crate" foam shape as is shown in FIGS. 2 and 2a in which the lowered domains 20 are valleys or crease points formed in the top surface 18 in both cross sectional directions with elevated domains 19 providing peaks. In this configuration, as the pressure-reducing layer 14 is initially compressed, only the elevated domains 19 are compressed, thereby providing a low resistance to the initial compressive force. The compressive force is increased, the lowered domains 20 are also compressed thereby providing a greater resistance to further compression. The elevated domains 19 and lowered domains 20 also provide crease points in the valleys extending across the pressure-reducing layer 14 in substantially right-angled relationship to each other so that the bending of a comparatively thick foam in a multiplicity of directions is facilitated. It will be readily understood that a foam so contoured will reduce interface pressure better i.e., provide a greater resistance than a standard planar foam pad, especially when the pressure to the pressure-reducing layer 14 is not evenly applied over the entire surface 18. As can be seen in FIGS. 2, 3, 5 and 7, a predetermined pattern of permanent creases in foam or the like or in a bubble wrap or other air-containing component will provide the desired contouring.

Ideally, the dressing will be constructed and arranged so as to allow custom cutting to patient specifications. Therefore, in a preferred form, the pressure reducing layer 14 should not be so dense as to prohibit cutting with surgical scissors. Foam density can be calculated according to ASTM Guidelines by determining the mass and volume of a representative sample. In addition, the thickness of the dressing should not be so great as to preclude secure placement over the wound. Therefore, the ideal embodiment of the concept will result from a careful alignment of layer 14 thickness with density. In one example, an ester based polyurethane foam with a nominal 6 lb/cu.ft. density at a thickness of 0.75 inch was found to be conformable, provided the desired cushioning and was easily cut to fit different wound shapes.

Figure 5:
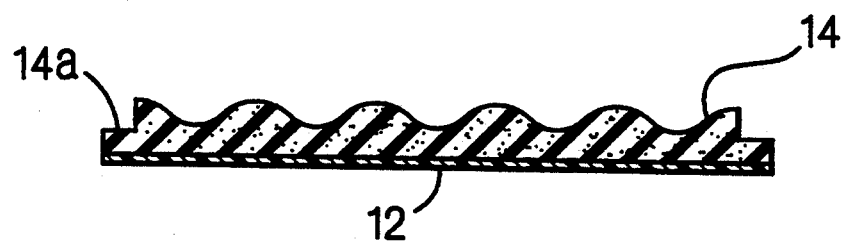
FIG. 5 is a cross-sectional view taken along line 5—5 of FIG. 4 to further illustrate the relatively thin, tape-down foam area referred in FIG. 4.
Figure 6:
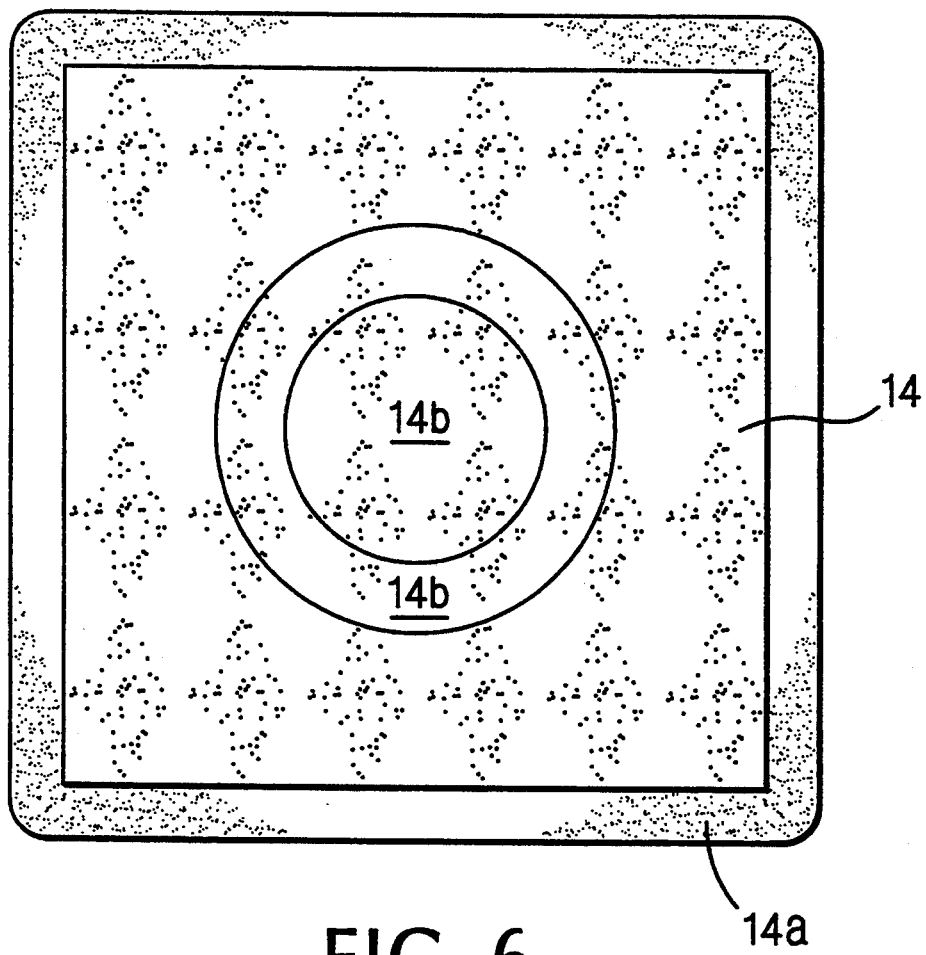
FIG. 6 is a schematic plan view of the top surface of an alternative form of the invention.
Figure 7:
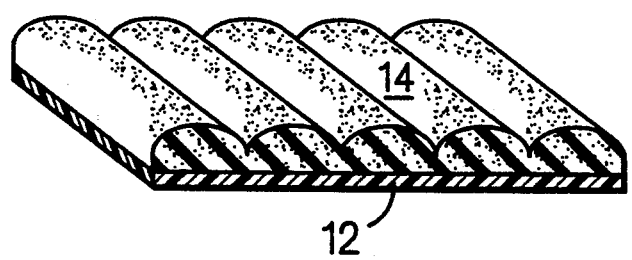
FIG. 7 is a perspective view illustrating yet another alternative form of the invention.

Referring now to FIGS. 4 and 5, a version somewhat similar to that of FIGS. 1 and 2 is shown. However, this version includes a layer 14 formed to include a relatively thin tape-down area 14a. The pressure reducing (foam) layer 14 has been modified to provide a thinner edge for ease of taping the dressing in place. This feature allows for more secure placement of the dressing and also reduces bulkiness in the tape area. Those skilled in the art will appreciate that the square design showed in FIG. 4 could be modified for specific wound shapes. Also, as shown in FIG. 6, the pressure reducing layer 14 could be perforated so as to allow removal of layer 14 just over the wound site. The occlusive layer 12 would remain intact over the wound and layer 14 would still provide cushioning around the wound while minimizing the bulk directly over the wound.

The above examples and disclosure are intended to be illustrative and not exhaustive. These examples and description will suggest many variations and alternatives to one of ordinary skill in the art. All these alternatives and variations are intended to be included within the scope of the attached claims. Those familiar with the art may recognize other equivalents to the specific embodiments described herein which equivalents are also intended to be encompassed by the claims attached hereto.

What is claimed is as follows:

1. An occlusive pressure-reducing dressing comprising in combination:
   (a) an occlusive, wound-contacting layer comprised of a biologically compatible polymer; and
   (b) a pressure-reducing layer that reduces the transmission of compressive forces with a progressive rate of resistance such that there is a low resistance to initial compression and provides increased resistance to greater compressive forces thereafter, having a bottom surface attached to the occlusive layer, the pressure-reducing layer comprised of air-containing material, the pressure-reducing layer having a top surface shaped in a contour that provides said progressive rate of resistance to said compressive forces applied to the pressure-reducing layer and which allows the pressure-reducing layer to conform to curved surfaces.

2. The dressing of claim 1 wherein the air-containing material comprises a foam.

3. The dressing of claim 1 wherein the air-containing material comprises an air-entrapping film.

4. The dressing of claim 1 wherein the perimeter of the pressure-reducing layer is cut thinner than the bulk of said layer to form an edge that accepts tape for securing to the skin of a patient.

5. The dressing of claim 1 wherein the biologically compatible polymer is selected from the group consisting of hydrogels and hydrocolloids.

6. The dressing of claim 5 wherein the hydrogel is a polyvinylalcohol/polyvinylpyrrolidone based hydrogel.

7. The dressing of claim 1, further comprising means, attached to the bottom surface of the pressure-reducing layer, for securing the dressing to a surface.

8. The dressing of claim 7 wherein the means for securing the dressing comprises an adhesive.

9. The dressing of claim 8 whereas means for securing the dressing comprises an adhesive border disposed around an outer periphery of the bottom surface of the pressure reducing layer.

10. The dressing of claim 1 wherein the top surface of the pressure-reducing layer is shaped to include a plurality of depressed portions on the top surface of the pressure-reducing layer.

11. The dressing of claim 10 wherein the depressed portions are arranged as a plurality of creases across the top surface of the pressure-reducing layer.

12. The dressing of claim 11 wherein at least some of the plurality of creases are arranged in a substantially right-angled orientation to the other of the plurality of creases.

13. A wound dressing, comprising:
   (a) a wound-contacting layer; and (b) a pressure-reducing layer that reduces the transmission of compressive forces with a progressive rate of resistance such that there is a low resistance to initial compression and provides increased resistance to greater compressive forces thereafter having a bottom surface joined to the wound-contacting layer, the pressure-reducing layer having a top surface with a non-planar contour having at least one peak and at least one valley, wherein the top surface contour allows the pressure-reducing layer to provide said variable rate of resistance to said compressive forces applied thereto.

14. The wound dressing of claim 13, further comprising means, attached to the pressure-reducing layer, for securing the dressing to a surface.

15. The wound dressing of claim 13, wherein a portion of the pressure-reducing layer is reduced in thickness at a predetermined location for facilitating securing the dressing to a surface.

16. The wound dressing of claim 13, wherein a portion of the pressure-reducing layer has an entire thickness of the layer removed at a predetermined location of the layer.

17. The wound dressing of claim 13, wherein the pressure-reducing layer comprises a solid material having air permeations homogeneously formed therethrough.

18. The wound dressing of claim 17, wherein the solid material comprises an air-containing foam.

19. The wound dressing of claim 13, wherein a portion of an entire thickness of the pressure-reducing layer is removed over the approximate area of the wound, the portion being of a predetermined shape.

20. The wound dressing of claim 19, wherein the predetermined shape of the pressure-reducing layer removed is circular.

* * * * *